United States Patent
Desai (10) Patent No.: US 11,589,931 B2
(45) Date of Patent: Feb. 28, 2023

(54) SURGICAL ROBOTIC SYSTEM AND METHOD FOR TRANSITIONING CONTROL TO A SECONDARY ROBOT CONTROLLER

(71) Applicant: Verb Surgical Inc., Santa Clara, CA (US)

(72) Inventor: Jignesh Desai, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 221 days.

(21) Appl. No.: 16/984,704

(22) Filed: Aug. 4, 2020

(65) Prior Publication Data

US 2022/0039889 A1 Feb. 10, 2022

(51) Int. Cl.
*A61B 34/00* (2016.01)
*B25J 9/16* (2006.01)
*A61B 34/30* (2016.01)

(52) U.S. Cl.
CPC .......... *A61B 34/25* (2016.02); *B25J 9/1602* (2013.01); *A61B 2034/301* (2016.02); *A61B 2034/302* (2016.02)

(58) Field of Classification Search
CPC .......... A61B 34/25; A61B 2034/301; A61B 2034/302; A61B 2017/00119;
(Continued)

(56) References Cited

U.S. PATENT DOCUMENTS

2015/0293779 A1* 10/2015 Gamer ............... G06F 11/2033
718/108
2019/0000578 A1 1/2019 Yu
(Continued)

FOREIGN PATENT DOCUMENTS

EP 1131004 B1 10/2009
WO 2012170256 A1 12/2012
(Continued)

OTHER PUBLICATIONS

Butner, Steven E., and Moji Ghodoussi. "Transforming a surgical robot for human telesurgery." IEEE Transactions on Robotics and Automation 19.5 (2003): 818-824.
(Continued)

*Primary Examiner* — Bao Long T Nguyen
(74) *Attorney, Agent, or Firm* — Lempia Summerfield Katz LLC (57) ABSTRACT

A robotic surgical system and method are disclosed for transitioning control to a secondary robotic arm controller. In one embodiment, a robotic surgical system comprises a user console comprising a display device and a user input device; a robotic arm configured to be coupled to an operating table; a primary robotic arm controller configured to move the robotic arm in response to a signal received from the user input device at the user console; and a secondary robotic arm controller configured to move the robotic arm in response to a signal received from a user input device remote from the user console. Control over movement of the robotic arm is transitioned from the primary robotic arm controller to the secondary robotic arm controller in response to a failure in the primary robotic arm controller. Other embodiments are provided.

20 Claims, 6 Drawing Sheets

(58) Field of Classification Search
CPC .. A61B 2017/00216; A61B 2034/2051; A61B 2034/2055; A61B 2034/2059; A61B 34/37; B25J 9/1602; B25J 9/1674; B25J 9/1689; B25J 3/00; B25J 13/06; G05B 23/0289–0291; G05B 2219/14114; G05B 2219/2234

See application file for complete search history.

(56) References Cited

U.S. PATENT DOCUMENTS

| | | | |
|---|---|---|---|
| 2019/0083186 A1* | 3/2019 | Zietlow | A61B 34/37 |
| 2019/0201135 A1 | 7/2019 | Shelton, IV et al. | |
| 2020/0205922 A1 | 7/2020 | Cone | |
| 2021/0220064 A1* | 7/2021 | Kottenstette | A61B 34/77 |

FOREIGN PATENT DOCUMENTS

| | | |
|---|---|---|
| WO | 2018006046 A1 | 1/2018 |
| WO | 2019055125 A1 | 3/2019 |

OTHER PUBLICATIONS

International Search Report and the Written Opinion for International Patent Application PCT/US2020/044885 dated Apr. 27, 2021.

* cited by examiner

SURGICAL ROBOTIC SYSTEM AND METHOD FOR TRANSITIONING CONTROL TO A SECONDARY ROBOT CONTROLLER

TECHNICAL FIELD

The subject technology generally relates to robotics and surgical systems, and more specifically to system architectures and components of a surgical robotic system for minimally invasive surgeries.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. In robotic MIS systems, it may be desirable to establish and maintain high positional accuracy for surgical instruments supported by the robotic arms.

Existing robotically-assisted surgical systems usually consist of a surgeon console that resides in the same operating room as the patient and a patient-side cart with four interactive robotic arms controlled from the console. Three of the arms hold instruments such as scalpels, scissors, or graspers, while the fourth arm supports an endoscope camera. In order to reposition the patient during a surgical procedure, surgical staff may have to undock the instruments/arms, reposition the arms/patient cart, and re-dock the instruments/arms.

SUMMARY

In some aspects, a surgical robot disclosed herein comprises a user console, a primary controller configured to control the surgical robot responsive to a first input from the user console, and a secondary controller configured to control the surgical robot responsive to a second input remote from the user console. The secondary controller is configured to receive communication from the primary controller, and control of the surgical robot is transitioned to the secondary controller from the primary controller in response to a failure of communication from the primary controller.

In some variations, the primary controller comprises a first mediator and the secondary controller comprises a second mediator. The communication from the primary controller comprises heartbeat messages sent by the first mediator at a predetermined rate. The failure of communication from the primary controller is detected when the second mediator fails to receive one or more heartbeat messages. The primary controller further comprises a supervisor process configured to inform the first mediator whether the primary controller is in a functional state, while the first mediator is configured to send the heartbeat message to the second mediator only when the primary controller is in the functional state. The primary controller comprises a first plurality of processes for controlling the surgical robot, and the secondary controller comprises a hibernated copy of the first plurality of processes. Transitioning the control of the surgical robot to the secondary controller comprises activating the hibernated copy of the first plurality of processes for controlling the surgical robot. The primary controller is further configured to receive state information from the surgical robot when controlling the surgical robot. Transitioning the control of the surgical robot to the secondary controller comprises routing the state information from the surgical robot to the secondary controller.

In some variations, the surgical robot further comprises a backup controller configured to receive heartbeat messages at a predetermined rate from the secondary controller when the secondary controller is controlling the surgical robot, and the control of the surgical robot is transitioned to the backup controller from the secondary controller in response to missing one or more heartbeat messages. The secondary controller comprises a second plurality of processes for controlling the surgical robot, while the backup controller comprises a hibernated copy of the second plurality of processes, and transitioning the control of the surgical robot to the backup controller comprises activating the hibernated copy of the second plurality of processes for controlling the surgical robot. The secondary controller is configured to receive state information from the surgical robot when controlling the surgical robot, and transitioning the control of the surgical robot to the backup controller comprises routing the state information from the surgical robot to the backup controller. The backup controller is further configured to instruct a power distribution component to turn off power to the secondary controller.

In some aspects, a robotic method disclosed herein comprises controlling movement of a surgical robot by a primary robot controller based on input from a first input device; receiving heartbeat messages from a primary robot controller by a secondary robot controller, while the primary robot controller is controlling the surgical robot; responsive to failing to receive one or more heartbeat messages, transitioning control of the surgical robot to the secondary robot controller; and controlling movement of the surgical robot by the secondary robot controller based on input from a second input device different from the first input device.

In some variations, failing to receive the heartbeat messages from the primary robot controller is caused by at least one of a failure of power supply, a failure of hardware, a failure of software and a failure of communication in the primary robot controller. Transitioning control of the surgical robot comprises bringing processes in the secondary robot controller out of hibernation, wherein the processes in the secondary robot controller are copies of processes in the primary robot controller for controlling of the surgical robot. Transitioning control of the surgical robot further comprises routing communication from the surgical robot to the secondary robot controller instead of the primary robot controller. Responsive to determining that the secondary robot controller is unable to control movement of the surgical robot, transitioning control of the surgical robot to a backup robot controller coupled to the secondary input device, wherein transitioning control of the surgical robot to a backup robot controller comprises bringing processes in the backup robot controller out of hibernation and routing the communication from the surgical robot to the backup controller instead of the secondary robot controller.

In some aspects, a surgical robotic system disclosed herein comprises one or more robotic arms mounted to a surgical table, a user console including a first user interface device remote to the surgical table, a primary controller configured to control the one or more robotic arms in response to input received from the first user interface device at the user console; and means for transitioning control of the one or more robotic arms from the primary controller to a secondary controller positioned within the surgical table in response to a failure in the primary controller, wherein the secondary controller is configured to maneuver the one or more robotic arms in response to input received from a second user interface device coupled to the one or more robotic arms and the secondary controller.

DETAILED DESCRIPTION

Examples of various aspects and variations of the subject technology are described herein and illustrated in the accompanying drawings. The following description is not intended to limit the invention to these embodiments, but rather to enable a person skilled in the art to make and use this invention.

System Overview

Disclosed herein is a robotically-assisted surgical system, which is a software-controlled, electro-mechanical system, designed for surgeons to perform minimally-invasive surgery (MIS). The surgical robotic system may be comprised of three major subsystems: a surgeon subsystem—the user console (surgeon console or surgeon bridge), a central control subsystem—the control tower, and a patient subsystem—the table and robotic arms. A surgeon seated in a surgeon seat of the user console may control the movement of compatible instruments using master user input devices (UIDs) and foot pedals. The surgeon can view a three-dimensional (3D) endoscopic image on a high-resolution open stereo display, which provides the surgeon the view of the patient anatomy and instrumentation along with icons, apps, and other user interface features. The user console may also provide an option for immersive display using a periscope, which can be pulled from the back of the surgeon seat.

The control tower can function as the control and communication center of the surgical robotic system. It may be a mobile point-of-care cart housing a touchscreen display, and include computers that control the surgeon's robotically-assisted manipulation of instruments, safety systems, a graphical user interface (GUI), an advanced light engine (also referred to as a light source), and video and graphics processors, among other supporting electronic and processing equipment. The control tower can also house third-party devices like an electrosurgical generator unit (ESU), and insufflator and $CO_2$ tanks.

The patient subsystem may be an articulated operating room (OR) table with, for example, up to four integrated robotic arms positioned over the target patient anatomy. The robotic arms of the surgical system may incorporate a remote center design, i.e., each arm pivots about a fixed point in space where the cannula passes through a patient's body wall. This reduces lateral movement of the cannula and minimizes stresses at the patient's body wall. A suite of compatible tools can be attached/detached from an instrument driver mounted to the distal end of each arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints. An endoscope can be attached to any arm and provide the surgeon with the high resolution, three-dimensional view of the patient anatomy. The endoscope can also be used endoscopically (hand-held) at the start of a surgery and then be mounted on any one of the four arms. Additional accessories such as trocars (also called sleeves, seal cartridge, and obturators) and drapes may be needed to perform procedures with the surgical robotic system.

The surgical robotic system can be used with an endoscope, compatible endoscopic instruments, and accessories. The system may be used by trained physicians in an operating room environment to assist in the accurate control of compatible endoscopic instruments during robotically-assisted urologic, gynecologic and other laparoscopic surgical procedures. The system also allows the surgical staff to reposition the patient by adjusting the table without undocking the robotic arms during urologic, gynecologic and other laparoscopic surgical procedures. The compatible endoscopic instruments and accessories for use with the surgical system are intended for endoscopic manipulation of tissue including grasping, cutting, blunt and sharp dissection, approximation, ligation, electrocautery, and suturing.

Figure 1:
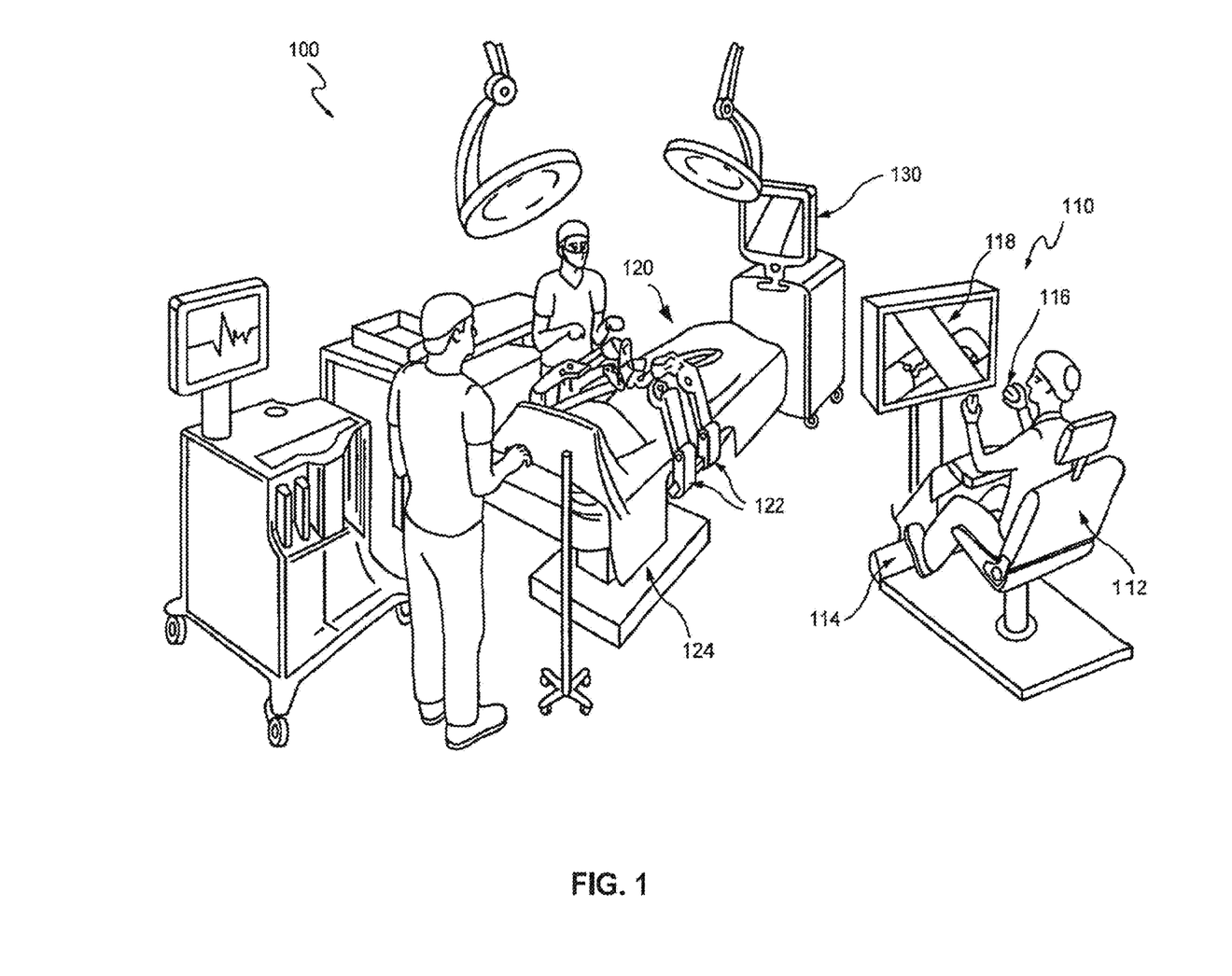
FIG. 1 is a diagram illustrating an example operating room environment with a surgical robotic system, in accordance with aspects of the subject technology.

Turning now to the drawings, FIG. 1 is a diagram illustrating an example operating room environment with a surgical robotic system 100, in accordance with aspects of the subject technology. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors (e.g., scalpels, scissors, or graspers) are attached to the distal ends of the robotic arms 122 for executing a surgical procedure. The robotic arms 122 are shown as table-mounted, but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control the robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Non-sterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The table 124 can be repositioned intraoperatively. For safety reasons, all tool tips should to be in view and under active control by the surgeon at the user console 110. Instruments that are not under active surgeon control must be removed, and the table feet must be locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

System Architecture

Figure 2:
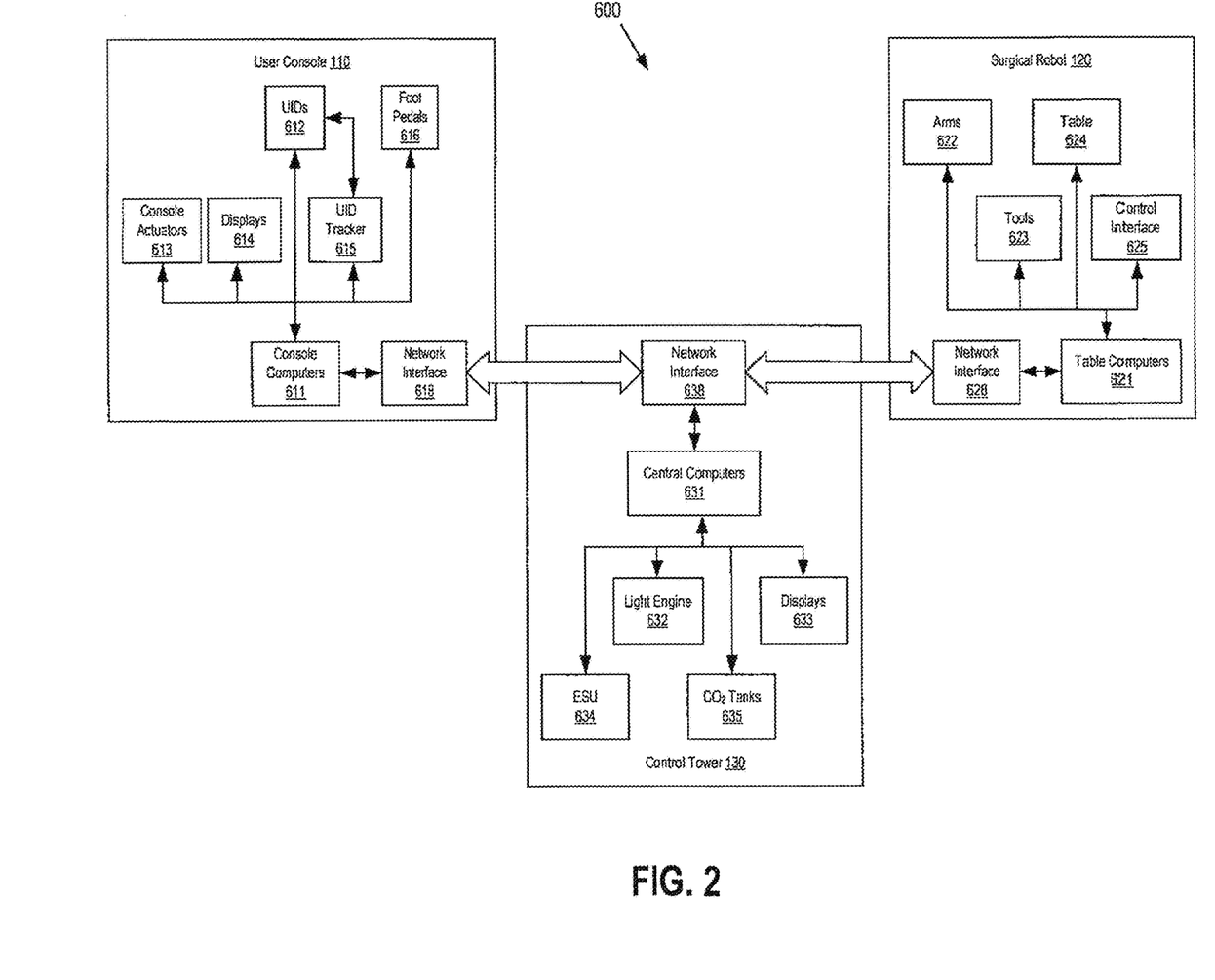
FIG. 2 is a block diagram illustrating exemplary hardware components of a surgical robotic system, in accordance with aspects of the subject technology.

FIG. 2 is a block diagram illustrating exemplary hardware components of a surgical robotic system 600, in accordance with aspects of the subject technology. The exemplary surgical robotic system 600 may include a user console 110, a surgical robot 120, and a control tower 130. The surgical robotic system 600 may include other or additional hardware components; thus, the diagram is provided by way of example and not a limitation to the system architecture.

As described above, the user console 110 comprises console computers 611, one or more UIDs 612, console actuators 613, displays 614, a UID tracker 615, foot pedals 616, and a network interface 618. A user or surgeon sitting at the user console 110 can adjust ergonomic settings of the user console 110 manually, or the settings can be automatically adjusted according to user profile or preference. The manual and automatic adjustments may be achieved through driving the console actuators 613 based on user input or stored configurations by the console computers 611. The user may perform robot-assisted surgeries by controlling the surgical robot 120 using two master UIDs 612 and foot pedals 616. Positions and orientations of the UIDs 612 are continuously tracked by the UID tracker 615, and status changes are recorded by the console computers 611 as user input and dispatched to the control tower 130 via the network interface 618. Real-time surgical video of patient anatomy, instrumentation, and relevant software apps can be presented to the user on the high-resolution 3D displays 614 including open or immersive displays.

Unlike other existing surgical robotic systems, the user console 110 disclosed herein may be communicatively coupled to the control tower 130 over a single fiber optic cable. The user console also provides additional features for improved ergonomics. For example, both an open and immersive display are offered compared to only an immersive display. Furthermore, a highly-adjustable seat for surgeons and master UIDs tracked through electromagnetic or optical trackers are included at the user console 110 for improved ergonomics. To improve safety, eye tracking, head tracking, and/or seat swivel tracking can be implemented to prevent accidental tool motion, for example, by pausing or locking teleoperation when the user's gaze is not engaged in the surgical site on the open display for over a predetermined period of time.

The control tower 130 can be a mobile point-of-care cart housing touchscreen displays, computers that control the surgeon's robotically-assisted manipulation of instruments, safety systems, graphical user interface (GUI), light source, and video and graphics computers. As shown in FIG. 2, the control tower 130 may comprise central computers 631 including at least a visualization computer, a control computer, and an auxiliary computer, various displays 633 including a team display and a nurse display, and a network interface 638 coupling the control tower 130 to both the user console 110 and the surgical robot 120. The control tower 130 may also house third-party devices, such as an advanced light engine 632, an electrosurgical generator unit (ESU) 634, and insufflator and $CO_2$ tanks 635. The control tower 130 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 comprises an articulated operating table 624 with a plurality of integrated arms 622 that can be positioned over the target patient anatomy. A suite of compatible tools 623 includes tools 623 that can be attached to or detached from the distal ends of the arms 622, enabling the surgeon to perform various surgical procedures. The surgical robot 120 may also comprise a control interface 625 for manual control of the arms 622, table 624, and tools 623. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 622 includes four arms mounted on both sides of the operating table 624, with two arms on each side. For certain surgical procedures, an arm mounted on one side of the table can be positioned on the other side of the table by stretching out and crossing over under the table and arms mounted on the other side, resulting in a total of three arms positioned on the same side of the table 624. The surgical tool can also comprise table computers 621 (such as a table adapter controller 700, which will be discussed below) and a network interface 628, which can place the surgical robot 120 in communication with the control tower 130.

Network Topology

Figure 3:
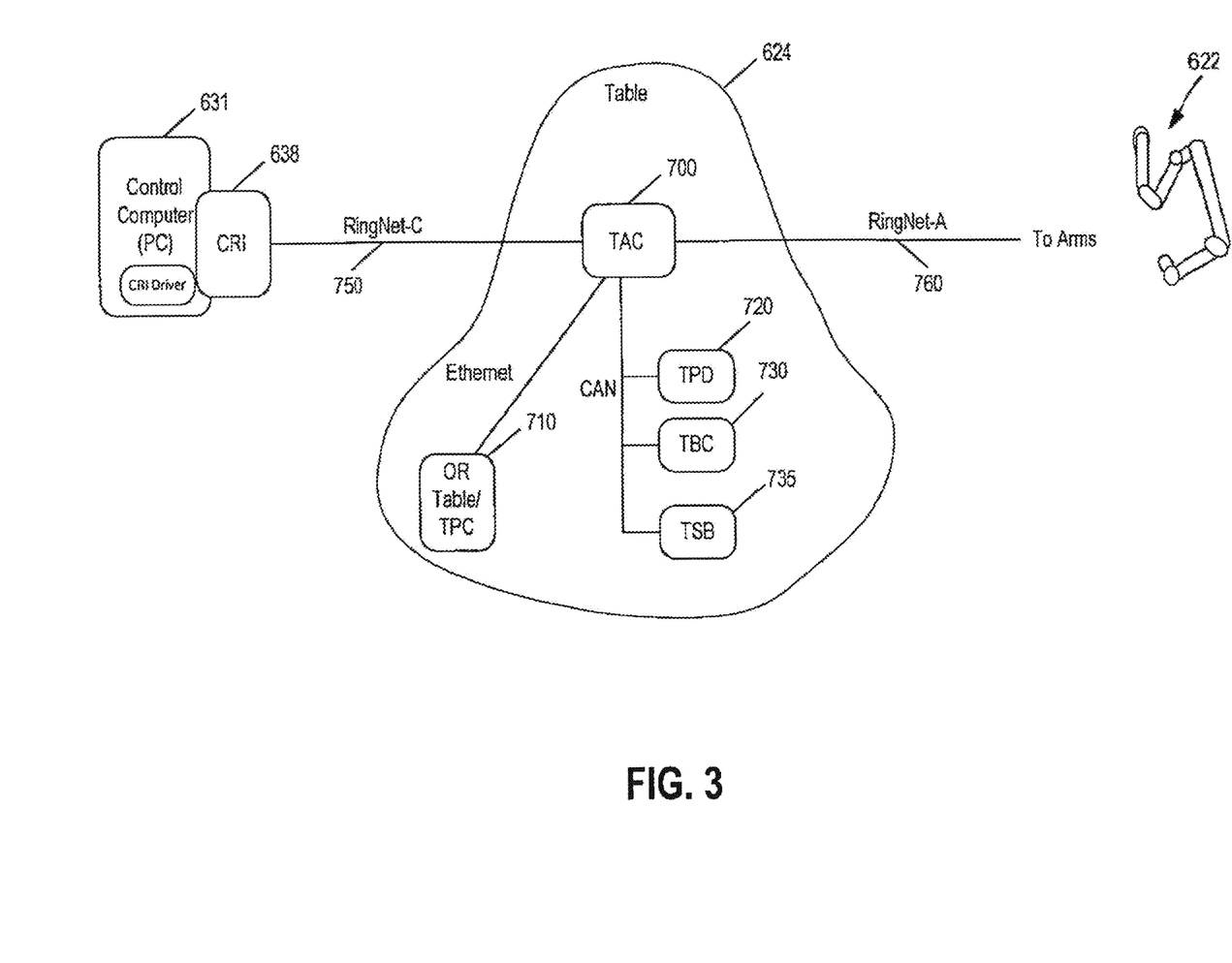
FIG. 3 is an illustration of a network topology of an embodiment.

In one embodiment, the control tower, the table controller, and the robotic arms communicate with each other over a network, such as a ring network, although other types of networks can be used. FIG. 3 is an illustration of a network topology of an embodiment. As shown in FIG. 3, the control computer 631 of the control tower uses a controller RingNet interface (CRI) 638 to communicate with the table computer (here, a table adapter controller (TAC) 700, which is also referred to herein as the "base controller") using a protocol designated herein as RingNet-C, with "C" referring to the "controller RingNet interface." The TAC 700 communicates with the robotic arms 622 using a different protocol designated herein as RingNet-A, with "A" referring to "arms." As shown in FIG. 3, the TAC 700 can also be in communication with a cluster of components (sometimes referred to herein as "the TAC cluster") of the table 624. For example, in this embodiment, the table 624 is articulated and has a drive motor controlled by a table pivot controller (TPC) 710 to tilt, move, etc. the table top. As also shown in FIG. 3, a table power distribution board (TPD) 720, a table base controller board (TBC) 730, and a table speaker board (TSB) 735 are in communication with the TAC 700 via a controller area network (CAN). Of course, other components and network protocols now existing or developed in the future can be used. The various table components in the TAC cluster will sometimes be referred to as table endpoints.

Each robotic arm in this embodiment includes a plurality of nodes between adjacent links. As used herein, a "node" can generally refer to a component that communicates with a controller of the robotic surgical system (e.g., the TAC 700). A "node," which will sometimes be referred to herein as a "joint module," can be used for actuating one link of the robotic arm with respect to another (e.g., by using a motor to move a series of pulleys and a series of bands connecting the pulleys to facilitate four-bar linkage movement). In response to commands from an external controller (discussed in more detail below), the nodes can be used to articulate the various links in the robotic arm to manipulate the arm for a surgical procedure. Examples of nodes include, but are not limited to, one or more of the following: a single motor (e.g., a servomotor, a pivot-link motor, a joint motor, and a tool drive motor), a dual motor (e.g., with a differential gear drive to combine the individual motor outputs), a wireless tool interface (e.g., a tool wireless board), a position sensor (e.g., an encoder that measures displacement of the arm links/segments), a force/torque sensor, an input/output board, a component that monitors power and/or communication links, or any other component that can receive/transmit data. A node can also include various electronics, such as, but not limited to, a motor controller/driver, signal processors, and/or communications electronics on a circuit board.

It should be noted that any of the controllers can be implemented in any suitable manner. For example, a controller can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. A controller can be configured with hardware and/or firmware to perform the various functions described below and shown in the flow diagrams. More generally, a controller (or module) can contain "circuitry" configured to perform various operations. As used herein, the term "circuitry" can refer to an instruction processor, such as a Central Processing Unit (CPU), microcontroller, or a microprocessor; or an Application Specific Integrated Circuit (ASIC), Programmable Logic Device (PLD), or Field Programmable Gate Array (FPGA); or a collection of discrete logic or other circuit components, including analog circuit components, digital circuit components or both; or any combination thereof. Circuitry may include discrete interconnected hardware components or may be combined on a single integrated circuit die, distributed among multiple integrated circuit dies, or implemented in a Multiple Chip Module (MCM) of multiple integrated circuit dies in a common package, as examples. Accordingly, "circuitry" may store or access instructions for execution or may implement its functionality in hardware alone.

The control PC (master controller) 631 can communicate information with the robotic arms 622 or with the components (e.g., the TPD 720, the TBC 730, and the TSB 735) in the TAC cluster. In operation, the control PC 631 sends a frame of information to the TAC 700, and an FPGA in the TAC 700 determines whether to route that frame to the TAC cluster or to the robotic arms 622. In one embodiment, the communication between the control PC 631 and the robotic arms 622 occurs is in real time (or near real time), while the communication with the various components in the cluster connected to the TAC 700 can occur in pseudo- or non-real time. Because the robotic arms 622 are interacting with the patient, it is preferred that the command/response communication between the control PC 631 and the various nodes (e.g., DSP motor controllers) of the robotic arms 622 be unimpeded, with little or no latency and with minimum jitter. In some embodiments, the arms 622s may send an error message if they do not receive communication from the control PC 631 in an expected amount of time. As used herein, a communication occurs in real time if the communication is received by a deadline set for receipt of that communication. Near real time refers to a communication that may be receive outside of the deadline due to a transmission delay but is, nonetheless, acceptable.

In contrast, the communication between the control PC 631 and the TAC cluster, while important, is not as urgent. For example, hardware in the table base controller (TBC) 730 may detect that the angle of the table has changed (e.g., by detecting a change in a gravity vector) or hardware in the table power distribution (TPD) board 720 may detect an overcurrent situation in one of the robotic arms 622, and software in those components can send an alert message back to the control PC 631 (e.g., which can display the alert on the graphical user interface of the control PC 631). Again, while this information is important, it can be communicated to the control PC 631 with more latency and/or jitter than would be acceptable in the command/response communication with the robotic arms 622. Such communications can be in non-real-time or pseudo-real-time (i.e., the communication does not need to be received by a certain deadline).

As noted above, the TAC frame and the arm frames can be separate frames, with the TAC 700 routing the frame to the robotic arms 622 or to the TAC cluster, as appropriate.

In one embodiment, the arm frame is a constant length frame that is transmitted by the control PC 631 every 4 kHz (250 microseconds), and the TAC frame is a variable length frame (because the control PC 631 may ask for information from the multiple end points in the TAC cluster, and the response length may vary). Again, in one embodiment, the arm frame is communicated on a real-time or near-real-time basis, and the TAC frame is communicated on a pseudo- or non-real-time basis. The arm and TAC frames can be time multiplexed in the fiber.

Transitioning Control

It is possible that a failure can occur in the communication channel between the user console and the TAC, which can result in the surgeon being unable to move the robotic arms with the user input devices at the user console. If this happens, the robotic arms can be frozen in place, perhaps inside the patient. This can lead to a hazardous situation, with the patient being entrapped by the robotic arms. The following embodiments can be used to detect such a failure and trigger/facilitate transition of control from the failed primary computer in the control tower to a secondary computer (and one or backups, if desired) in the TAC in order to mitigate patient entrapment due to loss of the primary computer.

In general, software mechanisms can be used to interact with facilitating electrical infrastructure to detect, trigger, and transition from remote operating mode (tele-operation) to standalone mode when primary and/or secondary robot control computers fail. Under normal operating conditions, the control-tower-hosted computer is the primary controller of the robots. Teleoperation (i.e., remote control or remote mode) is allowed only when this primary computer is healthy. A loss of the primary computer may lead to hazardous situations related to patient entrapment. A standby secondary computer with backup is provided as hardware mitigation for such situations. Detecting software, hardware and/or communication failures and triggering a switchover can be performed by hardware and/or software. For example, in one embodiment, the problem of detecting a failure and triggering a switch-over to the secondary computer is via a software mechanism, which in conjunction with hardware, collectively achieves a remote-to-standalone transition to the secondary computer. In one embodiment, if the secondary computer were to fail, a switch-over can be made to a backup computer. The following paragraphs describe one example implementation of this embodiment. It should be understood that this is merely an example and other implementations can be used.

Figure 4:
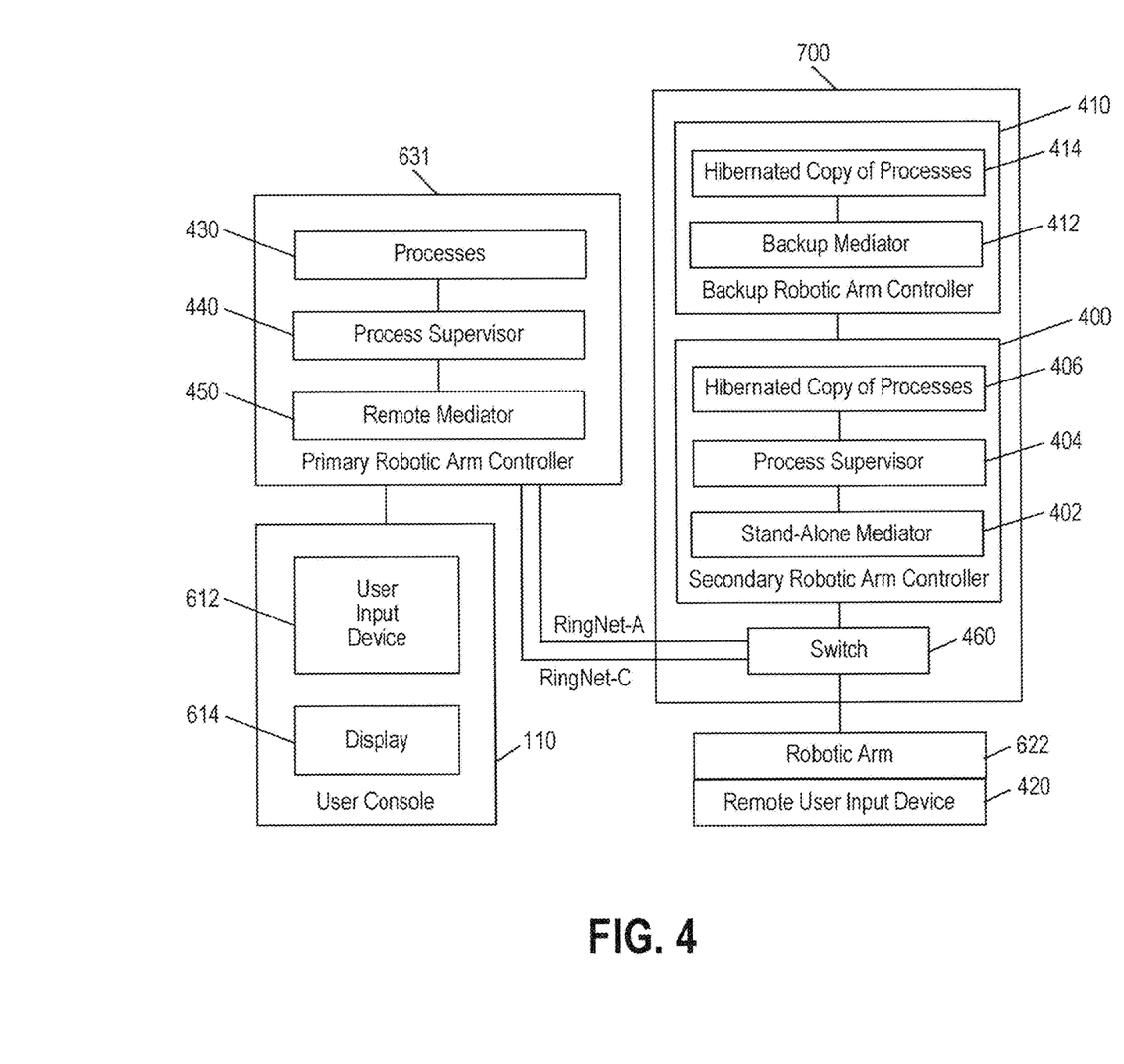
FIG. 4 is a block diagram of a surgical robotic system of an embodiment.

Returning again to the drawings, FIG. 4 is a block diagram of a surgical robotic system of an embodiment. Some of the components have been previously described in conjunction with the other drawings. As shown in FIG. 4, the overall system generally comprises the user console 110, a primary robotic arm controller 631 (which is sometimes referred to herein as a control PC and can be part of the control tower 130), a table adaptor controller (TAC) 700, and one or more robotic arms 622.

In this embodiment, the user console 110 comprises one or more user input devices 612 and a display 614. In teleoperation mode, a surgeon views a surgical site on the display 614 and uses the user input device 612 to manipulate the robotic arm 622. To do this, signals generated by manipulation of the user input devices 612 are sent to the primary robotic arm controller 631 in the control tower 130, which translates those signals into robot control signals which are sent to the TAC 700 (e.g., on RingNet-C). The TAC 700 then issues the robot control signals to the robotic arm 622 via RingNet-A to move them in accordance with the surgeon's movement of the user input device 612. Feedback and other information from the robotic arm 622 can be sent back to the primary robotic arm controller 631 via the TAC 700 (e.g., also on RingNet-C).

As mentioned above, it is possible for there to be a failure in the communication of messages between the primary robotic arm controller 631 and the TAC 700. If this happens, the surgeon would be unable to move the robotic arm 622 with the user input devices 612 at the user console 110, which can result in the patient being entrapped by the robotic arms 622. To address this situation, this embodiment allows control of the movement of the robotic arm 622 to be transferred from the primary robotic arm controller 631 to a secondary robotic arm controller 400 in the TAC 700 in response to a failure in the primary robotic arm controller 631. That way, the secondary robotic arm controller 400 can move the robotic arm 622 in response to a signal received from a user input device 420 that is remote from the user console 110 (e.g., a keypad on or near the robotic arm 622 or the operating table).

More specifically, as shown in FIG. 4, in this embodiment, the primary robotic arm controller 631 comprises a plurality of processes 430, a process supervisor 440, and a remote mediator 450. The processes 430, which can be implemented in software (e.g., computer-readable program code execute by a processor) and/or hardware, translate signals provided by the user input device 612 in the user console 110 into commands for movement of the robotic arm 622. The processes 430 can perform other functions as well, such as, but not limited to, reacting to feedback or other information from the robotic arm 622. The processor supervisor 440, which can be implemented as a QNX high availability manager (HAM), is a software and/or hardware module that monitors the functioning of the processes 430. The processor supervisor 440 informs the remote mediator 450 of the health of the processes 430 (i.e., whether or not the processes 430 are in a functional state). One or more of the processes may not be in the functional state, for example, if there is a power failure, a software failure, a hardware failure, a driver failure, a communication interface/channel failure etc.

Figure 5:
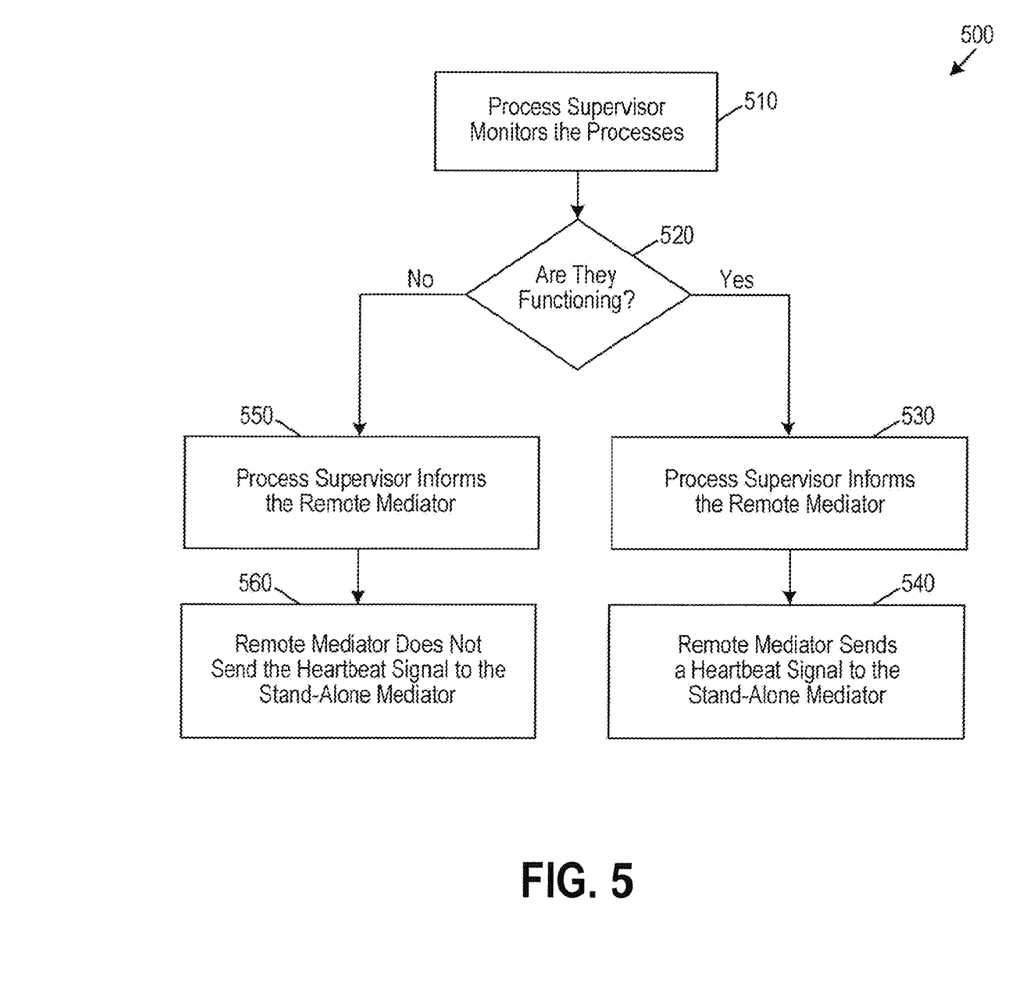
FIG. 5 is a flow chart of a method of an embodiment for detecting failure in a process in a primary robotic arm controller.

As shown in the flow chart 500 in FIG. 5, the processor supervisor 440 monitors the processes 430 (act 510) and determines if they are functioning (act 530). If the processes 430 are functioning, the processor supervisor 440 informs the remote mediator 450 (act 530), and the remote mediator 450 sends a message (referred to herein as a heartbeat message) to a corresponding stand-alone mediator 463 in the secondary robotic arm controller 400 (e.g., via RingNet-C) (act 540) at a constant rate (e.g., at predefined intervals). However, if the processes 430 are not functioning, the processor supervisor 440 informs the remote mediator 450 (act 550), and the remote mediator 450 does not send the heartbeat message to the stand-alone mediator 463 in the secondary robotic arm controller 400 (act 560).

Figure 6:
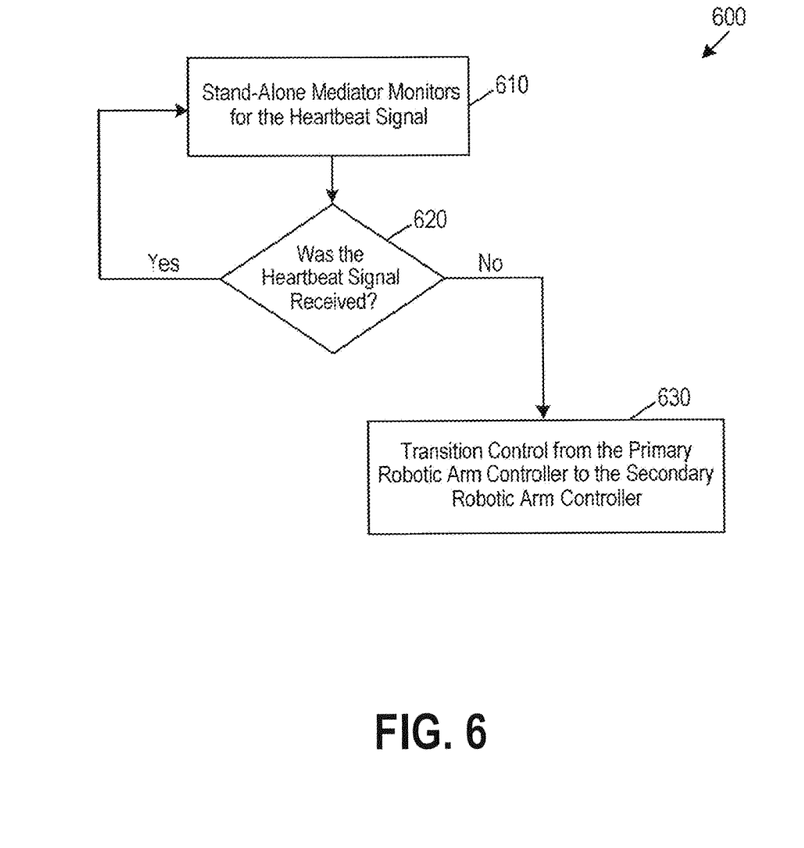
FIG. 6 is a flow chart of a method of an embodiment for monitoring for a heartbeat message.

As shown in the flow chart 600 in FIG. 6, the stand-alone mediator 463 monitors for the heartbeat message (act 610) and determines if the heartbeat message was received (act 620). If the heartbeat message was received, the secondary robotic arm controller 400 continues to monitor for the presence of a heartbeat message. However, if one or more heartbeat messages was not received (e.g., three heartbeat messages in a row), the stand-alone mediator 463 detects a failure in the primary robotic arm controller 631 and transitions control over the movement of the robotic arm 622 from the primary robotic arm controller 631 to the secondary robotic arm controller 400 (act 630).

This transition can be implemented in any suitable way. In one embodiment, in addition to the stand-alone mediator 402, the secondary robotic arm controller 400 comprises a hibernated copy of the processes 406 in the primary robotic arm controller 631. By both components having the same processes, both the primary robotic arm controller 631 and the secondary robotic arm controller 400 have the ability to move the robotic arm 622 in response to user input. In this embodiment, when the robotic surgical system powers on, both the processes 406, 430 are initialized, but the processes 406 in the secondary robotic arm controller 400 are put in a hibernation state. When the stand-alone mediator 402 detects a failure by not getting the heartbeat from the remote mediator 450, the stand-alone mediator 402 activates the hibernated processes 406, thereby bringing them out of the hibernation state. This allows the processes 406 to receive input from the remote user input device 420 to move the robotic arms 622. Again, this movement is made without involvement of the user console 110 or the primary robotic arm controller 631 in the control tower 130.

Other actions can be taken to transition control in addition to having the processes 406 in the secondary robotic arm controller 400 take over. For example, in normal operation, real-time information moves from the robotic arm 622 to the switch 460 via RingNet-A and then from the switch 460 to the robotic arm controller 631 via RingNet-C. This information can include feedback information regarding requested arm movement, and error signals, for example. If the primary robotic arm controller 631 is in the failed state, it may not be able to act on this information. So, in this situation, the information sent from the robotic arm 622 can be diverted to the secondary robotic arm controller 400 instead. In the embodiment shown in FIG. 4, the TAC 700 comprises a switch 460 (e.g., a field-programmable gate array or other programmable logic) that is configured to route information from the robotic arm 622 either to the primary robotic arm controller 631 or to the secondary robotic arm controller 400. When the secondary robotic arm controller 400 detects a failure in the primary robotic arm controller 631, the secondary robotic arm controller 400 programs the switch 460 to route the information from the robotic arm 622 to the secondary robotic arm controller 400.

Turning now to another feature, it is possible that there can be a failure in the processes 406 of the secondary robotic arm controller 400, which, just like failure in the primary robotic arm controller 631, can result in entrapment of a patient by the robotic arm 622. To address this possibility, the TAC 700 can comprise a backup robotic arm controller 410 having a backup mediator 412 and its own hibernated copy of the processes 414. (The primary robotic arm controller 631 and the backup robotic arm controller 410 can be implemented on two different systems on a module (SOMs).) A process supervisor 404 in the secondary robotic arm controller 400 monitor the health of the processes 406 in the secondary robotic arm controller 400 and determines if they are functioning. If the processes 406 are functioning, the processor supervisor 404 informs the stand-alone mediator 402, and the stand-alone mediator 402 sends a heartbeat message to the backup mediator 412 in the backup robotic arm controller 410. If the backup mediator 412 does not receive a heartbeat, it knows there is a failure and activates its copy of the processes 414. The table power distribution board (TPD) 720 (see FIG. 3) can be instructed to turn off the power domain to the secondary robotic arm controller 400 (a lack of a heartbeat message from the secondary robotic arm controller 400 to the TPD 720 can accomplish this). Since the switch 460 is already routing information from the robotic arm 622 to the TAC 700, no action is needed on the switch 460, and the information can be passed through the secondary robotic arm controller 400 to the backup robotic arm controller 410. Additional backup robotic arm controllers can be used.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

What is claimed is:

1. A surgical robot, comprising:
a user console;
a primary controller configured to control the surgical robot responsive to a first input from the user console; and
a secondary controller configured to control the surgical robot responsive to a second input remote from the user console;
wherein the secondary controller is configured to receive communication from the primary controller,
wherein control of the surgical robot is transitioned to the secondary controller from the primary controller in response to a failure of communication from the primary controller; and
wherein the primary controller comprises a first plurality of processes for controlling the surgical robot, wherein the secondary controller comprises a hibernated copy of the first plurality of processes.

2. The surgical robot of claim 1, wherein the primary controller comprises a first mediator, and wherein the secondary controller comprises a second mediator.

3. The surgical robot of claim 2, wherein the communication from the primary controller comprises heartbeat messages sent by the first mediator at a predetermined rate.

4. The surgical robot of claim 3, wherein the failure of communication from the primary controller is detected when the second mediator fails to receive one or more heartbeat messages.

5. The surgical robot of claim 3, wherein the primary controller further comprises a supervisor process configured to inform the first mediator whether the primary controller is in a functional state, and wherein the first mediator is configured to send the heartbeat message to the second mediator only when the primary controller is in the functional state.

6. The surgical robot of claim 1, wherein transitioning the control of the surgical robot to the secondary controller comprises activating the hibernated copy of the first plurality of processes for controlling the surgical robot.

7. The surgical robot of claim 1, wherein the primary controller is further configured to receive state information from the surgical robot when controlling the surgical robot.

8. The surgical robot of claim 7, wherein transitioning the control of the surgical robot to the secondary controller comprises routing the state information from the surgical robot to the secondary controller.

9. The surgical robot of claim 1, further comprising:
a backup controller configured to receive heartbeat messages at a predetermined rate from the secondary controller when the secondary controller is controlling the surgical robot, and
wherein the control of the surgical robot is transitioned to the backup controller from the secondary controller in response to missing one or more heartbeat messages.

10. The surgical robot of claim 9, wherein the secondary controller comprises a second plurality of processes for controlling the surgical robot,
wherein the backup controller comprises a hibernated copy of the second plurality of processes, and
wherein transitioning the control of the surgical robot to the backup controller comprises activating the hibernated copy of the second plurality of processes for controlling the surgical robot.

11. The surgical robot of claim 9, wherein the secondary controller is configured to receive state information from a robotic arm when controlling the robotic arm, and wherein transitioning the control of the robotic arm to the backup controller comprises routing the state information from the robotic arm to the backup controller.

12. The surgical robot of claim 9, wherein the backup controller is further configured to instruct a power distribution component to turn off power to the secondary controller.

13. A surgical robotic system, comprising:
one or more robotic arms mounted to a surgical table;
a user console including a first user interface device remote to the surgical table;
a primary controller configured to control the one or more robotic arms in response to input received from the first user interface device at the user console; and
means for transitioning control of the one or more robotic arms from the primary controller to a secondary controller positioned within the surgical table in response to a failure in the primary controller, wherein the secondary controller is configured to maneuver the one or more robotic arms in response to input received from a second user interface device coupled to the one or more robotic arms and the secondary controller;
wherein the means for transitioning control comprises (1) activation of a hibernated copy of a process for controlling the one or more robotic arms by the primary controller at the secondary controller or (2) state information received from the one or more robotic arms when controlling the one or more robotic arms being routed from the one or more robotic arms to the secondary controller.

14. The surgical robotic system of claim 13 wherein the control of the one or more robotic arms is transitioned to the secondary controller from the primary controller in response to a failure of communication from the primary controller.

15. The surgical robotic system of claim 14, wherein the primary controller comprises a first mediator, and wherein the secondary controller comprises a second mediator, wherein the communication from the primary controller comprises heartbeat messages sent by the first mediator at a predetermined rate.

16. The surgical robotic system of claim 15, wherein the primary controller further comprises a supervisor process configured to inform the first mediator whether the primary controller is in a functional state, and wherein the first mediator is configured to send the heartbeat message to the second mediator only when the primary controller is in the functional state.

17. The surgical robotic system of claim 14, wherein the failure of communication from the primary controller is detected when the secondary controller fails to receive one or more heartbeat messages.

18. The surgical robotic system of claim 13, wherein a mediator is configured to transition the control of the surgical robot to the secondary controller by the activation of the hibernated copy of the process for controlling the surgical robot.

19. The surgical robotic system of claim 13, further comprising:
a backup controller configured to receive heartbeat messages at a predetermined rate from the secondary controller when the secondary controller is controlling the one or more robotic arms, and
wherein the control of the surgical robot is transitioned to the backup controller from the secondary controller in response to missing one or more heartbeat messages.

20. A surgical robot, comprising:
a user console;
a primary controller configured to control the surgical robot responsive to a first input from the user console; and
a secondary controller configured to control the surgical robot responsive to a second input remote from the user console;
wherein the secondary controller is configured to receive communication from the primary controller,
wherein control of the surgical robot is transitioned to the secondary controller from the primary controller in response to a failure of communication from the primary controller;
a backup controller configured to receive heartbeat messages at a predetermined rate from the secondary controller when the secondary controller is controlling the surgical robot;
wherein the control of the surgical robot is transitioned to the backup controller from the secondary controller in response to missing one or more heartbeat messages; and:
wherein the secondary controller is configured to receive state information from the surgical robot when controlling the surgical robot, and wherein transitioning the control of the surgical robot to the backup controller comprises routing the state information from the surgical robot to the backup controller.

* * * * *